United States Patent
Su et al.

(10) Patent No.: US 10,999,141 B2
(45) Date of Patent: May 4, 2021

(54) MULTI-OBJECTIVE OPTIMIZATION METHOD FOR GROUNDWATER POLLUTION MONITORING NETWORK

(71) Applicant: CHINESE RESEARCH ACADEMY OF ENVIRONMENTAL SCIENCES, Beijing (CN)

(72) Inventors: Jing Su, Beijing (CN); Yuanyuan Sun, Beijing (CN); Beidou Xi, Beijing (CN); Mao Lin, Beijing (CN); Juan Li, Beijing (CN); Mingxia Zheng, Beijing (CN); Danfeng Ji, Beijing (CN); Chang Liu, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 0 days.

(21) Appl. No.: 16/849,389

(22) Filed: Apr. 15, 2020

(65) Prior Publication Data
US 2020/0252283 A1 Aug. 6, 2020

Related U.S. Application Data

(63) Continuation of application No. PCT/CN2018/092473, filed on Jun. 22, 2018.

(30) Foreign Application Priority Data

Oct. 16, 2017 (CN) .......................... 201710963185.X

(51) Int. Cl.
*G06F 15/173* (2006.01)
*H04L 12/24* (2006.01)
*G01N 33/18* (2006.01)

(52) U.S. Cl.
CPC ......... *H04L 41/0823* (2013.01); *G01N 33/18* (2013.01)

(58) Field of Classification Search
CPC .......................... H04L 41/0823; G01N 33/18
See application file for complete search history.

(56) References Cited

U.S. PATENT DOCUMENTS

| 7,767,093 | B2 * | 8/2010 | Frank | ................... | C02F 1/008 210/739 |
|---|---|---|---|---|---|
| 2007/0012628 | A1 * | 1/2007 | Frank | ................... | C02F 1/008 210/668 |
| 2017/0328878 | A1 * | 11/2017 | Xi | ..................... | G01N 33/18 |

* cited by examiner

*Primary Examiner* — Thanh T Nguyen
(74) *Attorney, Agent, or Firm* — CBM Patent Consulting, LLC

(57) ABSTRACT

A multi-objective optimization method for groundwater pollution monitoring network, which mainly includes four steps: groundwater numerical value simulation, groundwater vulnerability assessment, the establishment of the monitoring network optimization model, and the solving of the optimization model. The core of the method is to establish a multi-objective optimization model aimed at establishing the least monitoring wells, monitoring the maximum pollutant concentration, and monitoring the maximum regional vulnerability value. Solving the optimization model by the algorithm and considering the relationship between the quality error and the number of monitoring wells comprehensively to determine the well number and location of the monitoring network.

11 Claims, 2 Drawing Sheets

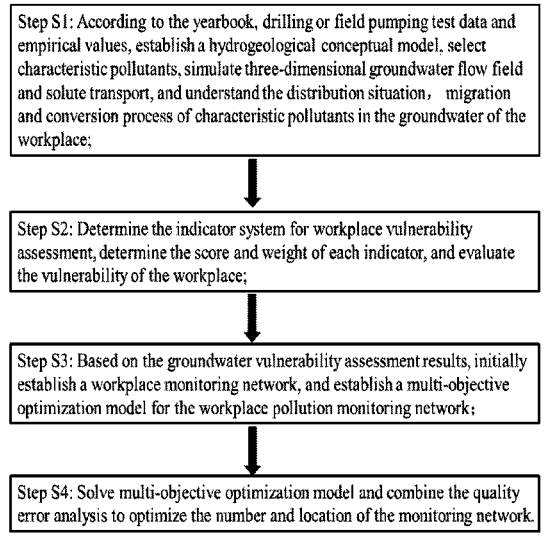

Step S1: According to the yearbook, drilling or field pumping test data and empirical values, establish a hydrogeological conceptual model, select characteristic pollutants, simulate three-dimensional groundwater flow field and solute transport, and understand the distribution situation, migration and conversion process of characteristic pollutants in the groundwater of the workplace;

Step S2: Determine the indicator system for workplace vulnerability assessment, determine the score and weight of each indicator, and evaluate the vulnerability of the workplace;

Step S3: Based on the groundwater vulnerability assessment results, initially establish a workplace monitoring network, and establish a multi-objective optimization model for the workplace pollution monitoring network;

Step S4: Solve multi-objective optimization model and combine the quality error analysis to optimize the number and location of the monitoring network.

FIG. 1

S201: According to the hydrogeological characteristics and pollution conditions of the groundwater source area, establish a groundwater vulnerability assessment indicator system suitable for workplaces containing groundwater sources;

S202: Uniformly quantify each indicator, establish scoring rules, and score each indicator according to the scoring rules;

S203: Determine the weight of each indicator;

S204: Perform groundwater vulnerability assessment of the workplace.

FIG. 2

MULTI-OBJECTIVE OPTIMIZATION METHOD FOR GROUNDWATER POLLUTION MONITORING NETWORK

This application is the continuation application of International Application PCT/CN2018/092473 filed on 22 Jun. 2018 which claims priority to Chinese Application No. CN201710963185.X filed on 16 Oct. 2017, the entire contents of each of which are hereby incorporated by reference.

TECHNICAL FIELD

The present invention belongs to the field of groundwater environment monitoring, and particularly relates to a multi-objective optimization method for groundwater pollution monitoring network based on the susceptibility and status of the groundwater pollution.

BACKGROUND ART

Groundwater is an important part of water resources and has gradually become an important source of drinking water in China. However, with the increase of human activities and the rapid development of social and economic production, groundwater resources are seriously polluted. In order to ensure the security of groundwater, it is necessary to establish a comprehensive groundwater monitoring network to obtain effective groundwater information.

Due to the concealment, deep burial depth, and slow water circulation, the self-purification ability of groundwater is rather poor. Once contaminated, it is difficult to recover, and the cost of repair is high. Therefore, prevention of groundwater pollution is more important than treatment, and it is necessary to monitor the areas with high pollution risks. Especially for the monitoring system of groundwater source area, while understanding the status of groundwater quality, monitoring the areas with high pollution risks can play a role of early warning. Decision makers can timely grasp pollution trend through monitoring data, formulate effective measures to prevent further spread of pollutants, minimize pollution hazards, and greatly ensure the safety of the wellhead.

At present, most groundwater monitoring networks have problems such as irrational spatial layout and redundancy or inadequacy of monitoring wells. Even if it costs a lot of money and resources, it cannot obtain sufficient and effective groundwater information. It is therefore necessary to optimize existing groundwater monitoring networks to establish groundwater monitoring systems with minimal cost to obtain adequate information. At present, there are numerous studies of optimization methods of groundwater monitoring networks at home and abroad, including statistical methods such as hydrogeological analysis, Kriging, Kalman filtering, and so on, optimization methods based on groundwater simulation, and combination of different methods, for example, multi-objective planning combined with geostatistical methods.

These methods are mainly based on hydrogeological conditions or the distribution of pollutants to optimize the monitoring network, and rarely consider the groundwater susceptibility. Some research on layout of monitoring wells based on groundwater vulnerability does not quantitatively determine the number and location of monitoring wells. Therefore, current research is difficult to quantitatively optimize the number and location of the monitoring network while considering groundwater vulnerability and pollution distribution.

CONTENTS OF THE INVENTION

In order to solve the above problems existing, the present invention provides a multi-objective optimization method for pollution monitoring network which is more suitable for groundwater source.

The multi-objective optimization method for groundwater pollution monitoring network provided by the present invention comprises: S1 According to the yearbook, drilling or field pumping test data and empirical values, establish a hydrogeological conceptual model, select characteristic pollutants, simulate three-dimensional groundwater flow field and solute transport, and get the distribution situation, migration and conversion process of characteristic pollutants in the groundwater of the workplace; S2 Determine the indicator system for workplace vulnerability assessment, determine the score and weight of each indicator, and evaluate the vulnerability of the workplace; S3 Based on the groundwater vulnerability assessment results, initially establish a workplace monitoring network, then establish a multi-objective optimization model for the workplace pollution monitoring network; S4 Solve multi-objective optimization model and combine the quality error analysis to optimize the well number and location of the monitoring network.

Compared with the prior art, the multi-objective optimization method for groundwater pollution monitoring network provided by the present invention has the following beneficial effects:

Know the groundwater polluting status in workplace through groundwater simulation, delineate the vulnerable area through groundwater vulnerability assessment, establish and solve the multi-objective optimization model with the goal of least number of monitoring wells, maximum sum of pollutant concentration monitored, and maximum sum of vulnerability scores at selected monitoring sites, to optimize all targets simultaneously and obtain the optimized well number and location of the monitoring network. The monitoring network optimized by this method can detect the most seriously polluted and the most vulnerably polluted areas, and improve the effectiveness and advancement of monitoring data.

DESCRIPTION OF FIGURES

In order to illustrate the embodiment of the present invention more clearly, the drawings used in the embodiment will be briefly described below.

FIG. 1 is a flowchart of a multi-objective optimization method for groundwater pollution monitoring network according to the embodiment of the present invention;

FIG. 2 is a detailed flowchart of groundwater vulnerability assessment.

SPECIFIC EMBODIMENTS FOR CARRYING OUT THE INVENTION

In order to make the objects, technical solutions, and advantages of the present invention more comprehensible, the present invention will be further described in details below with reference to specific embodiments and the accompanying drawings.

In order to solve the problem that the existing optimization method is hard to quantitatively optimize the monitoring network when considering the groundwater vulnerability, the present invention selects the multi-objective optimization method, and uses the groundwater vulnerability and pollutant concentration as decision variables in the multi-objective optimization model, thereby the groundwater vulnerability and pollution distribution are considered simultaneously, and analyzing the result of the multi-objective optimization model to quantitatively optimize the well number and location of the monitoring network.

As shown in FIG. 1, the multi-objective optimization method for groundwater pollution monitoring network provided by the present invention comprises:

S1. According to a yearbook, drilling or field pumping test data and empirical values, establish a hydrogeological conceptual model, select characteristic pollutants, simulate three-dimensional groundwater flow field and solute transport, and get the distribution situation, migration and conversion process of characteristic pollutants in the groundwater of the workplace;

Said hydrogeological conceptual model includes aquifer and topsoil layer. In one embodiment, the conceptual model in S1 is to generalize the geological layer into four layers, from top to bottom includes: topsoil layer, pore phreatic aquifer, pore weak confined aquifer, and pore confined aquifer; select nitrate as the characteristic pollutant according to the condition of the pollution source discharge and the groundwater quality monitoring data; construct the three-dimensional groundwater numerical model, and simulate the distribution of nitrate in the region and the future migration and transformation.

S2. Determine the indicator system for workplace vulnerability assessment, determine the score and weight of each indicator, and evaluate the vulnerability of the workplace;

As shown in FIG. 2, the step specifically includes:

S201: According to the hydrogeological characteristics and pollution conditions of the groundwater source area, establish a indicator system of groundwater vulnerability assessment suitable for workplaces containing groundwater sources;

well group, land use type and pollution source. The data of depth to water, aquifer medium, and so on can be obtained from local geological survey data or by drilling. Using the groundwater simulation software to simulate the groundwater flow field when pumped and unpumped water respectively, comparing the flow direction and flow velocity of the streamline under the two scenarios, and drawing the changed area of the groundwater flow field flowing to the water source under two scenarios by ArcGIS. The ratio of the area of variation range of the streamline when pumping water compared to when not pumping water to the well number in the range is impact range of the pumping well group. The land use type is obtained through analysising the land use map of the workplace. The indicator score of pollution source is given according to the pollutant discharge amount released per unit area, which is calculated based on the relevant data obtained from the yearbook and pollution source survey.

In S2, the essential vulnerability indicator score refers to the indicator score in the DRASTIC method, and the score grading standards of the special vulnerability indicators including impact range of pumping well group, land use type, and pollution source are shown in Table 2. Different land type regions set different scores; the pollution source indicator is graded according to emission amount of pollution source; the indicator score of the impact range of pumping well group is determined by two parts, firstly, the value is taken within 1 to 5 according to the size of the impact range, and then based on the evaluation result of the essential vulnerability, multiplied by the coefficient corresponding to the highest level of the essential vulnerability within the impact range of pumping well group (see Table 3), and the calculation formula is as follows: The indicator score of impact range of pumping well group=size score of impact range of pumping well group× coefficient

TABLE 2

Indicator categories and scoring standards

| Size of impact range of pumping well group/(km²/well) | | | | | | |
|---|---|---|---|---|---|---|
| <10⁻² | ≥10⁻²~1 | >1~2 | >2~3 | >3 | — | — |
| score 1 | 2 | 3 | 4 | 5 | | |

| land use type | | | | | | |
|---|---|---|---|---|---|---|
| grassland | woodland, wetland | waters | cultivated field | waste land | industrial mine | place of residence |
| score 2 | 4 | 5 | 6 | 7 | 8 | 10 |

| pollution source/(kg · hm⁻² · a⁻¹) | | | | | | |
|---|---|---|---|---|---|---|
| <50 | ≥50~100 | ≥100~150 | ≥150~200 | ≥250~300 | >300 | — |
| score 1 | 2 | 4 | 6 | 8 | 10 | |

S202: Uniformly quantify each indicator, establish scoring rules, and score each indicator according to the scoring rules;

S203: Determine the weight of each indicator;

S204: Perform groundwater vulnerability assessment of the workplace.

In one embodiment, the indicator system of vulnerability assessment in S2 is divided into essential vulnerability and special vulnerability. The indicators of essential vulnerability include depth to water, recharge, aquifer medium, topography and impact of the vadose zone media. The special vulnerability indicators include impact range of pumping

TABLE 3

Coefficient of different levels of essential vulnerability

| | vulnerability level | | | | |
|---|---|---|---|---|---|
| | lower | low | medium | high | higher |
| coefficient | 1.2 | 1.4 | 1.6 | 1.8 | 2.0 |

In S2, the weight of each indicator is determined by using an analytic hierarchy process, and the process includes stratifying the evaluation system, setting the groundwater vulnerability as the first layer, namely the target layer; and the second layer is the criterion layer, which includes two factors, essential vulnerability and special vulnerability respectively; and the third layer is the decision-making layer, and this layer includes the specific indicators of the essential vulnerability and special vulnerability; constructing a judgment matrix of indicators of each layer; performing single order and consistency test of each layer according to the judgment matrix; performing total order and consistency test of the layers; and the product of the weight of each indicator in the decision-making layer and the target weight of the corresponding criterion layer is the weight of each indicator on the groundwater vulnerability.

Weight sum of the scores and weights of each indicator using ArcGIS to get the vulnerability assessment results of the workplace. The vulnerability is divided into five levels: lower, low, medium, high and higher, according to the vulnerability score, and different levels of vulnerability are displayed in different colors in the ArcGIS to present a partition map of groundwater vulnerability.

S3. Based on the groundwater vulnerability assessment results, initially establish a workplace monitoring network, and establish a multi-objective optimization model for the workplace pollution monitoring network;

In one embodiment, the method for initially establishing the workplace monitoring network in S3 is: Determining the area and the initial density of each vulnerability level region according to the vulnerability assessment results, wherein the initial density of the monitoring wells required by different vulnerability levels is listed in Table 4. The number of monitoring wells initially set in the region with each vulnerability level is not less than the product of the area and density of the corresponding region, and the existing 6 monitoring wells and 34 pumping wells are integrated to form an initial monitoring network of 60 wells.

TABLE 4

| Initial density of monitoring wells with different vulnerability levels | | | | |
| --- | --- | --- | --- | --- |
| vulnerability levels | | | | |
| higher | high | medium | low | lower |
| M/(a/km²) ¼ | ⅑ | 1/16 | 1/25 | 1/100 |

The multi-objective optimization model for the monitoring network in S3 is: (1) the minimum number of monitoring wells; (2) the maximum sum of pollutant concentration monitored; and (3) the maximum sum of vulnerability scores at all selected monitoring sites. The specific formulas are: Objective functions are as follows:

$$\min Z_1 = \Sigma_{j \in J} \Sigma_{i \in Q_j} X_i \quad (1)$$

$$\max Z_2 = \Sigma_{j \in J} \Sigma_{i \in Q_j} V_i X_i \quad (2)$$

$$\max Z_3 = \Sigma_{j \in J} \Sigma_{i \in Q_j} Y_i X_i \quad (3)$$

Constrained functions are as follows:

$$N_j^* \geq N_j \geq 1, j \in J \quad (4)$$

$$N_j = \Sigma_{i \in Q_j} X_i, j \in J, i \in Q_j, Q_j \in I \quad (5)$$

$$N_j^* = [S_j \times M_j], j \in J \quad (6)$$

$$X_i = [0,1], i \in I \quad (7)$$

Wherein, $Z_1$ is the number of monitoring wells; $Z_2$ is the mass concentration of pollutants monitored, mg/L; $Z_3$ is vulnerability score at monitoring site; $Q_j$ is the set of location numbers of monitoring well in the j-th partition; Xi is a binary decision variable, indicating whether the i-th monitoring well is selected, the value is 1 when the monitoring well is selected, and 0 is not selected; $V_i$ is the groundwater vulnerability score at the i-th monitoring well location; $Y_i$ is the mass concentration of groundwater pollutants the i-th well monitored, mg/L; $N_j$ is the number of monitoring wells selected in the j-th partition; $S_j$ is the area of the j-th partition, km²; $M_j$ is the density of the monitoring wells corresponding to the groundwater vulnerability level of the j-th partition prokm²; $N_j^*$ is the upper limit of the number of monitoring wells in the j-th partition, and the value is the smallest integer greater than the product of $S_j$ and $M_j$; I is the set of location numbers of all monitoring well; and J is the set of partition numbers of regional vulnerability.

Wherein, constrained function $N_j^* \geq N_i \geq 1$, $j \in J$ constrains the maximum and minimum number of monitoring wells in each partition, ensuring that there are monitoring wells in each partition without over-aggregation.

S4. Solve multi-objective optimization model and combine the quality error analysis to optimize the well number and location of the monitoring network.

In one embodiment, the multi-objective optimization model in S4 is calculated by NSGA-II. The calculation process is: generate the initial population firstly, read the concentration data obtained from the solute transport simulation and the vulnerability score obtained from the vulnerability assessment to calculate the objective function values, which include the number of monitoring wells, the sum of pollutant concentration value monitored, and the sum of vulnerability scores at selected monitoring sites. Calculate the non-dominated sorting and focus distance of the corresponding population according to the calculated objective function values, select, cross, and mutate to generate the next child, merge the child and the parent population, perform the NSGA-II optimization iterative calculation until the maximum iteration number is reached, exit the cycle, and finally obtain the Pareto optimal solution designed by the multi-objective optimization for groundwater pollution monitoring network. The whole process is implemented by running code programmed by MATLAB.

The calculated Pareto optimal solution reflects the trade-off relationship between the number of monitoring wells and the vulnerability score and the nitrate concentration monitored. The solution results show appropriate range of the monitoring well number and optimal layout of the monitoring network for different number of monitoring wells within the numerical range.

The quality error analysis process in S4 is: according to the pollutant concentration (for example, nitrate concentration) at the optimal monitoring well location of different monitoring wells solved by NSGA-II, using ordinary Kriging method to calculate the concentration value of unknown nodes, and estimated spatial distribution of pollutants corresponding to the optimal layout scheme of different monitoring wells is obtained. Comparing with the total mass concentration of pollutants estimated by interpolation using monitoring concentration of all wells (such as nitrate concentration), calculating the corresponding quality error, fitting the relationship between the different well number and the quality error, and the corresponding quantity of the monitoring well within the acceptable error range is the recommended well number of optimized monitoring network. In one embodiment, after quality error analysis in S4, when within 15.00% is considered to be an acceptable quality error, the number of optimal monitoring wells is 12, and there is at least one monitoring well in each partition. The monitoring wells are mainly distributed in areas with high vulnerability and high nitrogen concentration of nitrate(s), which ensures the monitoring purpose and accuracy, and compared with the initial monitoring network which composed of 60 wells, the monitoring cost is reduced by 80%.

The Multi-objective optimization method for groundwater pollution monitoring network provided by the embodiment of the present invention can be applied to the optimization of the groundwater monitoring network with the groundwater source and the pollution source area.

The objects, the technical solutions and the beneficial effects of the present invention are described in detail by the above embodiments. However, the above is only the specific embodiments of the present invention, and is not intended to limit the present invention. Any modifications, equivalent substitutions, improvements, and so on made within the spirit and principles of the present invention are intended to be included within the scope of the present invention.

What is claimed is:

1. A multi-objective optimization method for groundwater pollution monitoring network, characterized in that, the method comprises the following steps:
   S1: according to a yearbook, drilling or field pumping test data and empirical values, establish a hydrogeological conceptual model, select characteristic pollutants, simulate three-dimensional groundwater flow field and solute transport, and get the distribution situation, migration and conversion process of characteristic pollutants in the groundwater of the workplace;
   S2: determine the indicator system for workplace vulnerability assessment, determine the score and weight of each indicator, and evaluate the vulnerability of the workplace;
   S3: based on the groundwater vulnerability assessment results, initially establish a workplace monitoring network, then establish a multi-objective optimization model for the workplace pollution monitoring network;
   S4: solve multi-objective optimization model and combine the quality error analysis to optimize the well number and location of the monitoring network;
   The method to initially establish monitoring network for workplace described in S3 is:
   determining the regional area and initial density of each vulnerability level according to the vulnerability assessment results, and the number of initial monitoring wells in the region with each vulnerability level is not less than the product of the area and initial density of corresponding region, and integrating the distribution of the established monitoring wells and pumping wells to form an initial monitoring network;
   the multi-objective optimization model for the monitoring network described in S3 includes three objective functions: (1) the minimum number of monitoring wells; (2) the maximum sum of pollutant concentration monitored; and (3) the maximum sum of vulnerability scores at selected monitoring sites.

2. The multi-objective optimization method for groundwater pollution monitoring network according to claim 1, characterized in that, S2 comprises:
   S201: according to the hydrogeological characteristics and results of pollution survey of the groundwater source area, establish a vulnerability assessment indicator system suitable for workplace in groundwater source area;
   S202: uniformly quantify each indicator, establish scoring rules of the indicators, and score each indicator according to the scoring rules;
   S203: determine the weight of each indicator;
   S204: perform groundwater vulnerability assessment of the workplace.

3. The multi-objective optimization method for groundwater pollution monitoring network according to claim 2, characterized in that, the indicator system of vulnerability assessment described in S201 includes essential vulnerability and special vulnerability; the indicators of essential vulnerability include: depth to water, recharge, aquifer medium, topography and impact of the vadose zone media, and the special vulnerability indicators includes impact range of pumping well group, land use type and pollution source.

4. The multi-objective optimization method for groundwater pollution monitoring network according to claim 3, characterized in that, the partition method of the impact range of pumping well group is:
   using groundwater simulation software to simulate the groundwater flow field of groundwater source area in pumped and non-pumped condition respectively, comparing the flow direction and flow velocity of the streamline under the two scenarios, drawing the changed area of the groundwater flow field flowing to the groundwater source area under two scenarios by ArcGIS, and the ratio of the area of variation range of the streamline when pumping water compared to when not pumping water to the well number in the range is the impact range of pumping well group.

5. The multi-objective optimization method for groundwater pollution monitoring network according to claim 3, characterized in that, the score of impact range of pumping well group in term of the scoring rules of indicators described in S202 is determined by the size of the impact range of pumping well group and the regional essential vulnerability, firstly, the value is taken within 1 to 5 according to the size of the range, and then multiplied by the coefficient corresponding to the highest level of the essential vulnerability within the impact range of pumping well group.

6. The multi-objective optimization method for groundwater pollution monitoring network according to claim 2, characterized in that, the score of pollution source in term of the scoring rules of the indicators described in S202 is given according to the pollutant amount released per unit area.

7. The multi-objective optimization method for groundwater pollution monitoring network according to claim 2, characterized in that, the weight of each indicator described in S203 is determined by analytic hierarchy process.

8. The multi-objective optimization method for groundwater pollution monitoring network according to claim 1, characterized in that, the specific formulas of the multi-objective optimization model for the monitoring network are:

objective functions are as follows:

$$\min Z_1 = \Sigma_{j \in J} \Sigma_{i \in Q_j} X_i \quad (1)$$

$$\max Z_2 = \Sigma_{j \in J} \Sigma_{i \in Q_j} V_i X_i \quad (2)$$

$$\max Z_3 = \Sigma_{j \in J} \Sigma_{i \in Q_j} Y_i X_i \quad (3)$$

constrained functions are as follows:

$$N_j^* \geq N_j \geq 1, j \in J \quad (4)$$

$$N_j = \Sigma_{i \in Q_j} X_i, j \in J, i \in Q_j, Q_j \in I \quad (5)$$

$$N_j^*=[S_j \times M_j], j \in J \qquad (6)$$

$$X_i=[0,1], i \in I \qquad (7)$$

wherein, $Z_1$ is the number of monitoring wells; $Z_2$ is the mass concentration of pollutants monitored, mg/L; $Z_3$ is vulnerability score at monitoring site; $Q_j$ is the set of location numbers of monitoring well in the j-th partition; Xi is a binary decision variable, indicating whether the i-th monitoring well is selected, the value is 1 when the monitoring well is selected, and 0 is not selected; $V_i$ is the groundwater vulnerability score at the i-th monitoring well location; $Y_i$ is the mass concentration of groundwater pollutants the i-th well monitored, mg/L; $N_j$ is the number of monitoring wells selected in the j-th partition; $S_j$ is the area of the j-th partition, km$^2$; $M_j$ is the density of the monitoring wells corresponding to the groundwater vulnerability level of the j-th partition, pro km$^2$; $N_j^*$ is the upper limit of the number of monitoring wells in the j-th partition, and the value is the smallest integer greater than the product of $S_j$ and $M_j$; I is the set of location numbers of all monitoring well; and J is the set of partition numbers of regional vulnerability.

9. The multi-objective optimization method for groundwater pollution monitoring network according to claim 1, characterized in that, the multi-objective optimization model described in S4 is used to obtain the optimal layout of monitoring wells under different well number conditions.

10. The multi-objective optimization method for groundwater pollution monitoring network according to claim 9, characterized in that, the multi-objective optimization model is calculated by NSGA-II, and based on the NSGA-II solution results, the optimized number and location of the monitoring network are determined combining with the quality error analysis.

11. The multi-objective optimization method for groundwater pollution monitoring network according to claim 1, characterized in that, said hydrogeological conceptual model generalizes aquifer and topsoil layer.

* * * * *